(12) United States Patent
Clerc

(10) Patent No.: US 10,213,289 B2
(45) Date of Patent: *Feb. 26, 2019

(54) BRONCHOSCOPIC LUNG VOLUME REDUCTION VALVE

(71) Applicant: BOSTON SCIENTIFIC SCIMED, INC., Maple Grove, MN (US)

(72) Inventor: Claude Clerc, Marlborough, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/433,568

(22) Filed: Feb. 15, 2017

(65) Prior Publication Data

US 2017/0156843 A1 Jun. 8, 2017

Related U.S. Application Data

(63) Continuation of application No. 14/992,415, filed on Jan. 11, 2016, now Pat. No. 9,597,174, which is a (Continued)

(51) Int. Cl.
*A61F 2/04* (2013.01)
*A61B 17/12* (2006.01)
(Continued)

(52) U.S. Cl.
CPC .......... *A61F 2/04* (2013.01); *A61B 17/12022* (2013.01); *A61B 17/12104* (2013.01); *A61B 17/12172* (2013.01); *A61F 2/24* (2013.01); *A61F 2/82* (2013.01); *A61F 2/90* (2013.01); *F16K 15/00* (2013.01); *F16K 99/0003* (2013.01); *A61B 2017/00575* (2013.01); *A61B 2017/00592* (2013.01); *A61B 2017/00597* (2013.01); *A61B 2017/00606* (2013.01); (Continued)

(58) Field of Classification Search
CPC .................................. A61F 2/20; A61F 2/203
USPC ...................................................... 623/9, 23.65
See application file for complete search history.

(56) References Cited

U.S. PATENT DOCUMENTS 5,662,713 A 9/1997 Andersen et al.
6,193,748 B1 * 2/2001 Thompson ....... A61B 17/12022
623/1.3
(Continued)

FOREIGN PATENT DOCUMENTS

EP 0864301 9/1998
WO 0238038 5/2002

*Primary Examiner* — Suzette J Gherbi
(74) *Attorney, Agent, or Firm* — Fay Kaplun & Marcin, LLP

(57) ABSTRACT

A valve to perform lung volume reduction procedures is described. The valve is formed of a braided structure that is adapted for endoscopic insertion in a bronchial passage of a patient's lung. The braided structure has a proximal end and a distal end and is covered with a non porous coating adapted to prevent flow of air into the. A constricted portion of the braided structure is used to prevent flow of air through a central lumen of the structure, and to define at least one funnel shaped portion. The funnel shaped portion blocks the flow of air towards the constriction, i.e. towards the core of the lung. At least one hole is formed in the braided structure to permit flow of mucus from the distal end to the proximal end, to be expelled out of the lungs.

13 Claims, 2 Drawing Sheets

Related U.S. Application Data continuation of application No. 11/250,968, filed on Oct. 14, 2005, now Pat. No. 9,265,605.

(51) Int. Cl.

| | | |
|---|---|---|
| *A61F 2/24* | (2006.01) | |
| *A61F 2/90* | (2013.01) | |
| *A61F 2/82* | (2013.01) | |
| *F16K 15/00* | (2006.01) | |
| *F16K 99/00* | (2006.01) | |
| *A61B 17/00* | (2006.01) | |
| *A61F 2/07* | (2013.01) | |
| *A61M 39/22* | (2006.01) | |
| *A61M 39/24* | (2006.01) | |

(52) U.S. Cl.
CPC ........... *A61B 2017/00615* (2013.01); *A61B 2017/00619* (2013.01); *A61F 2/07* (2013.01); *A61F 2002/043* (2013.01); *A61F 2210/0014* (2013.01); *A61F 2210/0057* (2013.01); *A61F 2220/0008* (2013.01); *A61F 2230/008* (2013.01); *A61F 2230/0078* (2013.01); *A61F 2250/001* (2013.01); *A61F 2250/0039* (2013.01); *A61M 39/22* (2013.01); *A61M 2039/244* (2013.01); *A61M 2039/248* (2013.01); *A61M 2210/1039* (2013.01); *F16K 2099/0088* (2013.01)

(56) References Cited

U.S. PATENT DOCUMENTS

| | | | |
|---|---|---|---|
| 6,692,494 B1 | 2/2004 | Cooper et al. | |
| 6,941,950 B2 * | 9/2005 | Wilson | A61F 2/2412 128/200.24 |
| 7,011,094 B2 * | 3/2006 | Rapacki | A61B 17/12022 128/200.24 |
| 9,265,605 B2 * | 2/2016 | Clerc | A61B 17/12022 |
| 2003/0070683 A1 | 4/2003 | Deem et al. | |
| 2005/0137518 A1 * | 6/2005 | Biggs | A61B 17/064 604/8 |
| 2005/0137712 A1 * | 6/2005 | Biggs | A61B 17/064 623/23.7 |
| 2005/0192526 A1 * | 9/2005 | Biggs | A61B 17/064 604/8 |
| 2007/0255394 A1 * | 11/2007 | Ryan | A61F 2/2412 623/1.24 |
| 2011/0251592 A1 * | 10/2011 | Biggs | A61B 17/064 604/514 |

\* cited by examiner

BRONCHOSCOPIC LUNG VOLUME REDUCTION VALVE

PRIORITY CLAIM

The present application is a Continuation of U.S. patent application Ser.No. 14/992,415 filed on Jan. 11, 2016, now U.S. Pat. No. 9,597,174; which is Continuation of U.S patent application Ser. No. 11/250,968 filed Oct. 14, 2005, now U.S. Pat. No. 9,265,605. The entire disclosures of these applications/patent are expressly incorporated herein by reference.

BACKGROUND

Emphysema is a chronic, progressive disease of the lungs which affects millions of Americans. Patients affected with emphysema have a difficult time breathing. Emphysema is not presently curable, but it can be treated. Emphysema often is a result of chronic infection or irritation of the bronchial tubes. The bronchial tubes extend from the windpipe to the lungs, and look like branches of a tree, with the branches becoming smaller and smaller until each one ends in a cluster of small air spaces in the lung, called alveoli. When the bronchi become irritated, some of the airways may be obstructed, trapping air in the lung beyond them. The walls of the tiny air spaces may become damaged and may tear. If the stretching and destruction of the walls of the alveoli continues, portions of the lungs may become enlarged, at the same time becoming less efficient in exchanging oxygen for carbon dioxide. Healthy portions of the lungs may be compressed by the diseased lung portions.

Lung volume reduction surgery is one treatment used to relieve the symptoms of emphysema. The surgery creates more room for the patients' lungs by removing portions of the overly distended diseased lung. Up to 20-30% of each lung may be removed to allow more space for the remaining portion of the lung to inflate. While not a cure for emphysema, the surgery does afford many patients the opportunity to lead healthier, more active lives. Lung volume reduction surgery (LVRS) has been shown to improve pulmonary function, exercise capacity, quality of life and survival rate in selected patients. However, LVRS is a major surgical procedure with complications and potential morbidity and mortality, and is not suited for patients that may be weak, or otherwise unable to undertake major surgery.

SUMMARY OF THE INVENTION

In one aspect, the present invention is directed to a valve to perform lung volume reduction procedures, which comprises a braided structure adapted for endoscopic insertion in a bronchial passage, the braided structure having a proximal end and a distal end, a non porous coating adapted to prevent flow of air through the braided structure, a constricted portion of the braided structure preventing flow of air through a tubular central lumen of said braided structure, and defining a funnel shaped portion thereof, and at least one hole of the braided structure adapted to permit flow of mucus from the distal end to the proximal end. The funnel shaped portion is adapted to prevent flow of air from the proximal end to the distal end.

In a different aspect, the invention is directed to a one way valve for a biological flow passage. The valve comprises an elongated braided structure sized for insertion in the biological flow passage, a portion of the braided structure forming a substantially tubular shell, the braided structure maintaining an expanded operative shape after being temporarily compressed, a non porous coating of the braided structure, a constricted portion of the elongated braided structure disposed between a proximal end and a distal end thereof, the constricted portion defining at least one funnel shaped region of the braided structure impeding flow towards the distal end, and at least one hole formed in the non porous coating, permitting a flow of fluid towards the proximal end.

DETAILED DESCRIPTION

Figure 1:
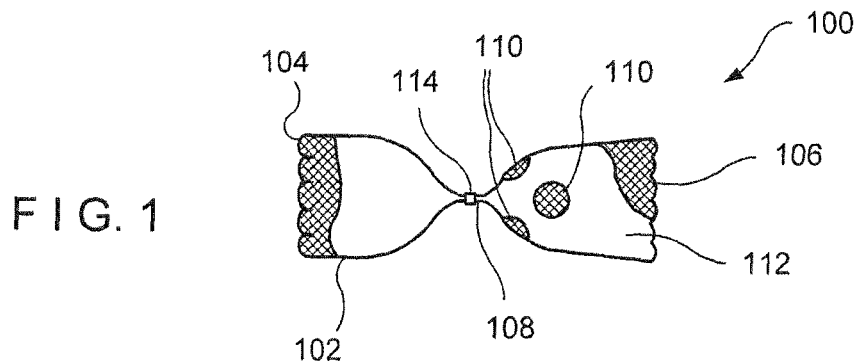
FIG. 1 is a diagram showing a first embodiment of a lung volume reduction valve according to the present invention.

The present invention may be further understood with reference to the following description and the appended drawings, wherein like elements are referred to with the same reference numerals. The present invention is related to medical devices used to provide unidirectional flow within biological flow passages. More specifically, the invention is related to medical devices used to control the flow of air and of mucus within the bronchial passages of a lung.

The exemplary embodiments of the present invention described herein relate to a one way valve which can be used to control the flow of a gas through a biological flow passage. In one example, the one way valve is used during lung volume reduction procedures which are often performed to alleviate the symptoms of emphysema. The one way valve may be used to restrict the flow of air reaching selected portions of the lungs, and at the same time to permit the flow of residual air and/or mucus and other fluids out of the lung. The exemplary valve according to the invention may comprise a braided tubular structure that is constricted at one end or in the middle. The braided structure may be covered with a non-porous coating, and may include openings or a secondary additional valve to allow passage of mucus across the valve.

Lung Volume Reduction (LVR) surgery is a medical technique used to treat emphysema. Although the procedure does not provide a cure to emphysema, it often alleviates the symptoms of the disease, and can significantly improve the quality of life of the patient. Emphysema results from chronic infection or irritation of the bronchial tubes, often caused by smoking, pollution, or other environmental and genetic factors. The bronchial tubes extend from the windpipe to the lungs, and look like branches of a tree, with the branches becoming smaller and smaller until each one ends in a cluster of small air spaces in the lungs, called alveoli. Emphysema causes some of the airways to become irritated and obstructed, trapping air in the lung beyond them. The walls of the alveoli in that region of the lung may become damaged and may tear. If the stretching and destruction of the walls of the air spaces continues, portions of the lungs may become enlarged, while at the same time becoming less efficient in exchanging oxygen for carbon dioxide.

In more advanced stages of the disease, healthy portions of the lungs may be compressed by the diseased and enlarged lung portions. The diaphragm of the patient also may be compressed by the enlarged lung tissue, so that taking every breath becomes a difficult and tiring process. The patient is faced with the dual challenges of breathing with only a portion of the lungs being functional, and with the additional difficulty of filling those functional portions with air against the pressure of the enlarged lungs. Conventional LVR surgery has been used to alleviate these difficulties. During the procedure, some of the diseased portions of the lung or lungs are removed via an open thoracotomy. About 20% to 30% of each lung may be removed in this major surgical operation, which is complex and has a high morbidity rate. The benefit of removing the enlarged, diseased portions of the lungs is that more room is left in the thoracic cavity where the remaining portion of each lung can expand.

Less intrusive procedures have been developed to achieve results similar to those of the open chest LVR procedures, without the associated complications and high morbidity rates. Principally, these less intrusive procedures involve depositing in the lungs devices that restrict the flow of air to the diseased portions of the lungs. Often, a bronchoscope is used to deliver the devices, without having to resort to cutting through the chest of the patient. The devices may be valves, which are placed in the bronchial passages leading to the affected portions of the lungs, or some other form of flow blockage, which prevents air from reaching the diseased portions. When a valve is used to prevent air from reaching selected portions of the lung, it is important to ensure that mucus can be expelled from those portions. A buildup of mucus in the lungs may lead to infections and other serious complications. Accordingly, it is desirable to provide valves that permit residual air and mucus to exit the lung, while preventing air from flowing therein.

Various devices and structures have been used in medical procedures to occlude the flow of a fluid in a biological flow passage or vessel. For example, it is often useful to restrict the flow of blood through a vein or artery. These devices generally consist of a braided metallic structure similar to a Wallstent© flexible tube, which is made impermeable with a polymeric coating. The flexible braided tube is constricted near its middle portion, into a shape similar to that of an hourglass. Alternatively, the braided tube may be constricted at one end, to form a cylindrical shell with one end terminating in a point. Examples of a flexible braided tube used for occluding the flow of a fluid through a blood vessel are described in U.S. Pat. No. 5,919,224, assigned to Schneider USA Inc., whose subject matter is hereby incorporated in its entirety by reference.

Structures similar to the one described above have been used also as filters placed in the bloodstream, for example to capture blood clots and prevent them from traveling through the patient's vascular system. U.S. Pat. No. 5,836,969 assigned to Boston Scientific describes one such filters, with an anchoring mechanism to retain it in place in a patient's vena cava. The anchoring mechanism consists of projecting wires and hooks, and serves to retain the filter against the force of the blood flowing in the vessel. In this manner the filter can be left in the patient's body for extended periods of time, without being displaced by the force of the flowing blood, or by the normal activities of the patient. The subject matter of the '969 patent is hereby incorporated by reference in its entirety.

The various embodiments of the present invention described herein provide for a one way valve used in bronchoscopic lung volume reduction procedures. In one more specific example, the valve consists of a braided structure with looped ends that is constricted in its middle. The structure may be fully or partially covered with a non-porous material which prevents the passage of air therethrough, so that the device may prevent the flow of air through the bronchial passages, at least in one direction. In one embodiment, some holes are formed at the distal end of the structure, to permit the passage of mucus out of the lungs through the distal part of the structure, then between the wall of the proximal part of the structure and the bronchial vessel, while at the same time preventing the inflow of air therein. An anti-microbial coating may also be applied to the device, to lessen the likelihood of an infection developing at the site of the valve.

FIG. 1 shows a diagram of an exemplary embodiment of a one way valve according to the present invention. The exemplary one way valve 100 comprises an elongated braided structure 102, which may be made preferably of a material such as Nitinol, MP35N, or Elgiloy. Other materials, preferably having shape memory properties and/or super-elastic properties, may also be used to construct the elongated braided structure 102. An example of another material may be a shape memory polymer. Such a plastically deformable material may be inserted into the bronchial tube using a tool or a balloon. The braided structure 102 may be designed to return to an operative, expanded configuration after being deformed by a constraining force. For example, the braided structure 102 may be compressed during deployment through a catheter, to fit through a small working channel. After deployment from the catheter, the braided structure 102 expands back to the original shape and dimensions, and occupies substantially the entire cross section of the bronchial channel where it is deployed.

A coating 112 may be applied to a portion or to substantially all of the surfaces of the braided structure 102. For example, the coating may comprise a non-porous polymeric material such as silicone, polyurethane, polyethylene terephthalate (PET), Polytetrafluoroethlylene (PTFE), etc. The non-porous material prevents the passage of fluids through the surfaces of the braided structure 102, so that it is effective in restricting the flow of air through the bronchial passage. The one way valve 100 has a distal end 106 which faces towards the alveoli of the lungs when placed within a bronchial passage, and a proximal end 104 which faces towards the trachea of the patient.

The braided structure 102 may have a substantially tubular elongated shell, similar to the structure of a braided stent, and may comprise a constricted portion 108 which is located longitudinally near the middle of the one way valve 100. The constricted portion 108 forms at least one funnel shaped portion of the braided structure 102, and in the embodiment shown in FIG. 1 forms two funnel shaped portions. Each of the funnel shaped portions prevents the flow of air in the direction towards the constricted portion 108. The narrowing of the constricted portion 108 may be achieved by applying an external force on the braided structure 102, such as with a band or a clip 114, or may be obtained by appropriate conventional manufacturing steps. The constricted portion 108 of the braided structure 102 also provides the desired one-way valve effect by substantially closing off the tubular channel formed within the braided structure 102.

When inserted into one of a patient's bronchial tubes, the proximal end 104 of the valve 100 faces toward the patent's trachea, while the distal end 106 faces toward the alveoli, i.e., the diseased portion of the lung. The outer diameter of the structure is selected to be slightly larger than the diameter of the bronchial tube. The valve 100 may also include a coating or an adhesive on the outside to allow it to adhere to the bronchial tube. Thus, when the patient inhales and air travels through the trachea toward the lung, the inhaled air that enters the bronchial tube having the valve 100 will be prevented from passing through the valve 100 and into the diseased portion of the lung. This inhaled air will enter the funnel shaped portion of the proximal end 104 and may cause the funnel shaped portion to radially expand causing the braided structure 102 to better contact the inner walls of the bronchial tube. This radial expansion may .improve the seal around the outside radius of the distal end 104. This outer tight seal and the inner constricted portion 108 allows little or no air to flow to the diseased portion of the lung. Thus, the valve 100 acts as an obstruction device when the patient inhales air. The exhale direction will be discussed in greater detail below.

The exemplary one way valve 100 shown in FIG. 1 may be compressed to a diameter that is smaller than its expanded, unconstrained diameter, and may be placed in the working channel of a small diameter catheter for delivery to the desired location. For example, a bronchoscope may be used to deliver the device to a bronchial passage between the patient's trachea and the alveoli found deep into the lungs. When the one way valve 100 is deployed from the catheter, it expands to its operative dimensions within the bronchi. For example, the shape memory properties of the materials used to form the braided structure 102 may promote the return to a preselected shape after being constrained. At least the proximal end 104 of the braided structure 102 expands to a diameter sufficient to encompass the internal dimensions of the bronchial passage, so that the flow of air may be restricted therethrough.

According to exemplary embodiments of the invention, the one way valve 100 may be made of polymeric or metallic filaments, which form the braided structure 102. The filaments may comprise a radiopaque component to improve the device's radiopacity, so that the operating surgeon is able to place the device in the patient's lungs more accurately. For example, if the braided structure 102 is made of a polymeric material, a radiopaque agent such as a metallic or ceramic powder may be included in the material during the manufacturing process. Alternatively, the polymer may include elements having a high atomic number such as iodine in its chemistry. If the braided structure is made out of metallic wires, a portion or all of these wires may have a radiopaque core. The constricted portion 108 may be constrained, for example, by a metallic ring 114, which can be of a radiopaque material. Other radiopaque devices and/or methods may also be used to provide the operating surgeon with a better view of the valve while it is being placed into the bronchial tubes, e.g., radiopaque markers and radiopaque paint. The proximal and distal ends 104, 106 of the braided structure 102 are designed to be atraumatic, to prevent injury to the trachea and to the bronchial passages when they are inserted into the lungs. For example, the extremities may be looped, so that there are no sharp strands or wires extending from the device, or they may be welded, also to form a smooth end surface.

One or more holes 110 are visible in the exemplary embodiment shown in FIG. 1. The holes are formed in the distal portion of the braided structure 102, and are designed to allow for residual air and mucus clearance from the lungs. The holes 110 may be formed in the non-porous coating 112 of the one way valve 100, while leaving the braids of the braided structure 102 unaffected. Alternatively, the holes 110 may be cut through the entire device, including the braided structure 102. The holes 110 are preferably located close to the constricted region 108 of the one way valve 100, away from the surrounding walls of the bronchial passage, or from the other biological structures in which the valve 100 may be inserted. The location of the holes 110 away from the inner walls of the passage avoids tissue ingrowth into the exposed braided structure, and makes the device more easily removable from the lungs of the patient even after a prolonged stay.

When a patient exhales or coughs the direction of the air and/or fluid flow will be from the alveoli through the bronchial passage to the trachea. If the valve 100 was simply a constriction device, this air/fluid flow would be eliminated in the same manner as described above for the inhale air flow. However, the valve 100 includes the holes 110 which transform the valve 100 into a one way valve allowing for air/fluid flow in the exhale direction as will be described. As described above, mucus and other fluids may build up in the diseased portion of the lung. This mucus must be allowed to be cleared from the lung. Similarly, even though little or no air will be entering the alveoli, there may be residual air in the alveoli because it is not physically possible during normal breathing to completely exhale all the air out of the lungs. In addition, because the diseased alveoli break down, there may be seepage of air from other alveoli into the alveoli connected to the blocked bronchial passage.

Thus, when exhaling or coughing, the air will flow from the alveoli to the funnel shaped portion of the distal end 106 of the valve 100. As described above for the proximal end 104, this air may cause the funnel portion to expand radially to form a tight seal between the distal end 106 and the bronchial passage. In a further exemplary embodiment, the distal end 106 may be sized slightly larger than the proximal end 104 in order to provide a continuous tight seal and securely anchor the valve 100 in the bronchial passage 100 or conversely. In addition, an increase in the length of the distal end 106 may also provide a better anchoring for the valve 100. The valve 100 may also include anchors so that the valve 100 is securely placed in the bronchial tube. In the exemplary embodiment of FIG. 1, the anchors may be placed in any position along the outer body of the valve 100 including in the area of the constricted portion 108.

In any case, as the air/fluid flows into the funnel portion of the distal end 106, it may then flow out of the holes 110 in the valve 100. This air/fluid will then be in the cavity between the constricted portion 108 and the bronchial passage. However, since the air/fluid is traveling in the exhale direction, this may cause the funnel portion of the proximal end 104 to radially contract allowing the air/fluid to flow out of the lung and be exhaled/discharged. Thus, the valve 100 acts as a constriction device for air flow in the inhale direction, but as an open valve for air/fluid flow in the exhale direction.

In a different embodiment, the constricted portion 108 may be located at a different location along the length of the valve 100. For example, the constriction may be formed near the distal end 106, to prevent the flow of air into the lung.

Figure 2:
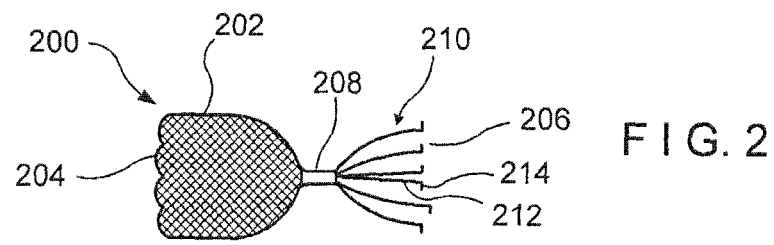
FIG. 2 is a diagram showing a second embodiment of a lung volume reduction valve according to the present invention, with an anchoring mechanism.

In general, the constriction may be formed at any location which allows the proximal end 104 to expand to a diameter sufficient to completely block the bronchial tube in which the device is placed. FIG. 2 shows an exemplary one way valve 200, in which the constriction 208 is formed near the distal end 206 of the device. In this exemplary embodiment, the constricted portion 208 forms only one funnel shaped portion of the device. When valve 200 is placed in a fluid moving towards the constriction 208 (i.e., air flowing in the inhale direction), the proximal end 204 is pushed radially outward by the flow, and causes the braided structure 202 to better contact the inner walls of the bronchial passage preventing air flow into the diseased portion of the lung. When air/fluid is traveling in the exhale direction, the funnel portion of the proximal end 204 may be radially constricted to allow the air/fluid to be exhaled/discharged.

Continuing with the exemplary embodiment of the FIG. 2, the distal potion 206 of the braided structure 202 has been replaced with an anchoring mechanism 210. The anchoring mechanism 210 may be, for example, similar to the anchoring mechanism described in U.S. Pat. No. 5,836,969, In one exemplary embodiment, the anchoring mechanism 210 may comprise a plurality of grasping wires such as shape memory wires 212, that may be made of Nitinol or of another suitable shape-memory material. The wires 212 may extend in a deployed configuration so that protrusions 214 formed at the tip of the wires 212 can engage the tissue of the bronchial passages in which the device is deployed. The anchoring mechanism 210 prevents undesired movement of the one way valve 200 from its desired location.

Figure 3:
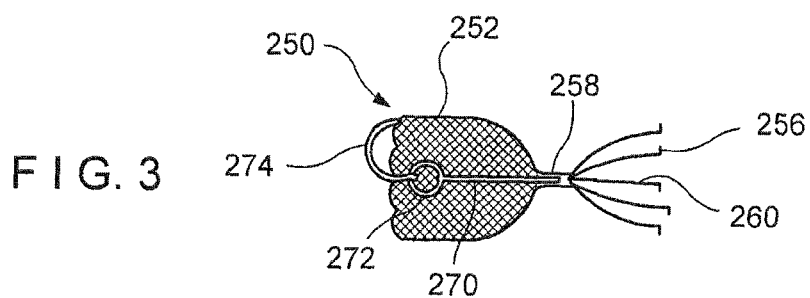
FIG. 3 is a diagram showing a third embodiment of a lung volume reduction valve according to the present invention, with a retrieval rod.

Another embodiment of the valve according to the present invention is shown in FIG. 3. Here, a retrieval mechanism is added to the proximal portion of the one way valve 250. An extending rod 270 passes through the tubular proximal portion of the braided structure 252, for example extending from the constricted portion 258. A loop or hook 272 may be provided at the proximal end of the extending rod 270, to facilitate retrieval of the device from the patient's lung. Repositioning of the device within the bronchial passage may also be accomplished by grasping it by the extension rod 270 and/or the loop 272. For example, forceps or other similar instruments may be used to endoscopically manipulate the one way valve 250.

In other embodiments, the retrieval mechanism may also include a retrieval loop disposed at the proximal end of the braided structure 252. For example, a retrieval loop 274 may be formed, extending from an edge of the braided structure 252 to another edge or to the extending rod 270. The retrieval loop 274 may be threaded around the proximal portion of the braided structure 252, and may comprise a plurality of loops and projections to improve the retrieval ability of the device. The loops and projections of the retrieval loop 274 may be polymeric or metallic, and may preferably comprise shape memory materials such as Nitinol.

Figure 4:
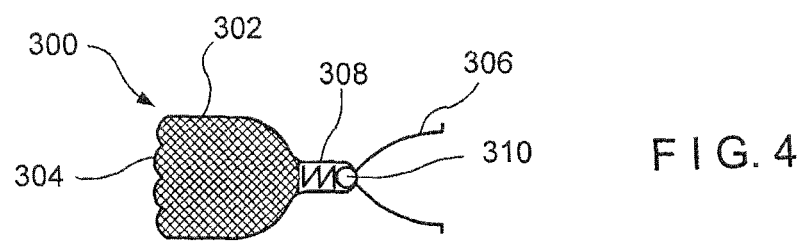
FIG. 4 is a diagram showing a fourth embodiment of a lung volume reduction valve according to the present invention, with a secondary one way valve.

In general, clearing of the mucus from the inner parts of the lung structure is likely to take place between the bronchi and the body of the valve. To facilitate the process, the exemplary embodiment shown in FIG. 4 comprises a secondary one way valve in the constricted portion. For example, the secondary one way valve 300 may comprise a valve body 310 disposed in the constricted portion 308, distally from the proximal end 304 of the expanded braided structure 302. The valve 310 may be a ball valve, a leaflet valve, a lip valve, a duckbill valve or a socket valve. Additional types of valves may also be used, to permit the flow of mucus from the lungs towards the trachea, in the direction towards the proximal end 304. The mucus may be expelled from the lungs through the secondary valve 310 by coughing and by the normal operation of the lungs.

Figure 5:
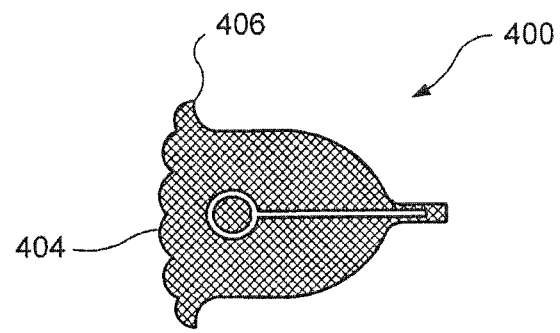
FIG. 5 is a diagram showing another embodiment of a lung volume reduction valve according to the present invention, with an exemplary anchoring structure.
Figure 6:
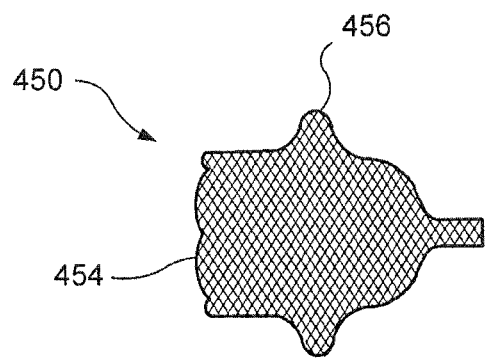
FIG. 6 is a diagram showing yet another embodiment of a lung volume reduction valve according to the present invention, with another anchoring structure.

Additional devices may be used to help anchor the one way valve within the bronchial passage or within other tubular structures of the patient's body. For example, as shown in FIG. 5, an anchoring flare 406 may be formed at the proximal end 404 of the braided structure 402. In this manner, the one way valve 400 may remain in place despite the movements caused by the daily activities of the patient, and despite the force applied by air moving through the lungs. In particular, the force of the air when the patient coughs may be very large, and may require a strong anchor. FIG. 6 shows another exemplary embodiment of an anchoring mechanism. In this case, the valve 450 has a bulge 456 formed on the braided structure 452. The bulge 456 and the flare 406 may be formed on the proximal part of the structure, as shown, or on the distal part of a structure similar to that shown in FIG. 1.

Figure 7:
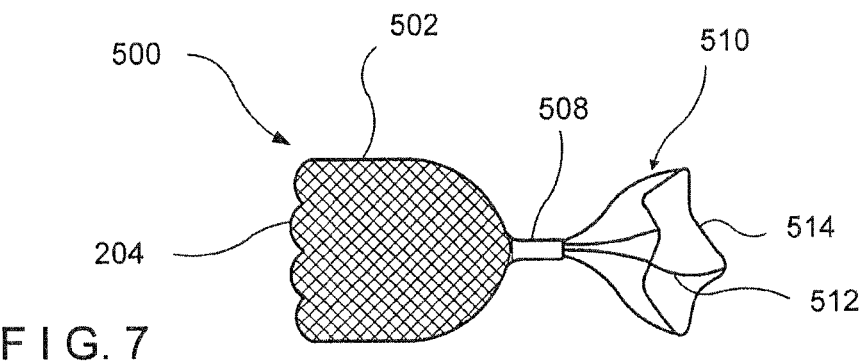
FIG. 7 is a diagram showing a different embodiment of a lung volume reduction valve according to the present invention, with a zig zag ring.

Yet another anchoring mechanism for an exemplary valve is shown in FIG. 7. In this exemplary embodiment, the one way valve 500 comprises a braided structure 502 having a constricted portion 508 at its distal end. An anchoring mechanism 510 is disposed at the distal end of the valve 500, and is designed to expand to a dimension substantially similar to the inner dimension of the bronchial passage. A zig zag ring 514 connected to the braided structure 502 by extending wires 512 may be used to anchor the device in place, when in the deployed configuration. A shape memory material such as Nitinol may be used to form the extending wires 412 and the zig zag ring 514, to ensure that the anchoring mechanism 510 expands to the desired shape and dimension after being compressed to a small size for deployed from a catheter or from a bronchoscope.

The present invention has been described with reference to specific exemplary embodiments. Those skilled in the art will understand that changes may be made in details, particularly in matters of shape, size, material and arrangement of parts without departing from the teaching of the invention. Additional organs may be treated by using the present invention, in addition to the lungs. Accordingly, various modifications and changes may be made to the embodiments without departing from the broadest scope of the invention as set forth in the claims that follow. The specifications and drawings are, therefore, to be regarded in an illustrative rather than a restrictive sense.

What is claimed is:

1. A one way valve for a biological flow passage, comprising:
   a braided structure extending longitudinally from a proximal end to a distal end, the braided structure movable from a constrained configuration to an expanded configuration so that, upon insertion of the braided structure in the biological flow passage, the braided structure is maintained in the expanded configuration, the braided structure including a constricted portion at the distal end thereof, the constricted portion closing off a channel of the braided structure to define a funnel shape which prevents flow towards the distal end;
   a non porous coating extending over a portion of the braided structure to prevent passage of fluids through the braided structure; and
   an anchoring portion extending distally from the distal end of the braided structure to anchor the braided structure within the biological flow passage.

2. The one way valve of claim 1, wherein the anchoring portion includes a plurality of grasping wires including tips configured to engage tissue of the biological flow passage.

3. The one way valve of claim 2, wherein the grasping wires retain a selected shape after being deformed during insertion.

4. The one way valve of claim 1, wherein the anchoring portion comprises a shape memory zig zag ring.

5. The one way valve of claim 1, further comprising a valve structure disposed within the constricted portion of the braided structure.

6. The one way valve of claim 5, wherein the valve structure includes one of a ball valve, a leaflet valve, a lip valve, a duckbill valve or a socket valve.

7. The one way valve of claim 1, further comprising a retrieval structure connected to the braided structure.

8. The one way valve of claim 7, wherein the retrieval structure includes an elongated rod extending proximally from the constricted portion through the channel of the braided structure.

9. The one way valve of claim 8, wherein the retrieval structure further includes one of a loop and a hook at a proximal end of the elongated rod.

10. The one way valve of claim 7, wherein the retrieval structure includes a retrieval loop extending proximally from the proximal end of the braided structure.

11. The one way valve of claim 1, wherein the braided structure is formed of one of Elgiloy, MP35N, Nitinol, another shape memory material and a super-elastic material.

12. The one way valve of claim 1, wherein the non porous coating is formed of one of silicone, polyurethane, PET and PTFE.

13. The one way valve of claim 1, wherein the constricted portion included one of a band and a clip mounted over the distal end of the braided structure.

* * * * *